United States Patent
Bender et al.

(10) Patent No.: US 7,345,203 B1
(45) Date of Patent: Mar. 18, 2008

(54) COST EFFECTIVE METHOD FOR SYNTHESIS OF TRIARYLAMINE COMPOUNDS FROM AN ANILINE AND AN ARYLCHLORIDE

(75) Inventors: Timothy P. Bender, Toronto (CA); Jennifer A. Coggan, Cambridge (CA)

(73) Assignee: Xerox Corporation, Norwalk, CT (US)

( * ) Notice: Subject to any disclaimer, the term of this patent is extended or adjusted under 35 U.S.C. 154(b) by 0 days.

(21) Appl. No.: 11/563,931

(22) Filed: Nov. 28, 2006

(51) Int. Cl.
*C07C 209/00* (2006.01)

(52) U.S. Cl. .................... 564/407; 564/405
(58) Field of Classification Search ............ 564/405, 564/407
See application file for complete search history.

(56) References Cited

U.S. PATENT DOCUMENTS

| | | | |
|---|---|---|---|
| 4,265,990 A | 5/1981 | Stolka et al. | |
| 5,648,542 A | 7/1997 | Goodbrand et al. | |
| 5,654,482 A | 8/1997 | Goodbrand et al. | |
| 5,705,697 A | 1/1998 | Goodbrand et al. | |
| 5,723,669 A | 3/1998 | Goodbrand et al. | |
| 5,723,671 A | 3/1998 | Goodbrand et al. | |
| 5,902,901 A | 5/1999 | Goodbrand et al. | |
| 6,235,938 B1 * | 5/2001 | Hartwig et al. | 564/407 |
| 6,730,448 B2 | 5/2004 | Yoshino et al. | |
| 6,958,204 B2 * | 10/2005 | Tanaka et al. | 430/133 |
| 2004/0086794 A1 | 5/2004 | Yamada et al. | |
| 2005/0234272 A1 | 10/2005 | Goodbrand et al. | |
| 2006/0111582 A1 | 5/2006 | Goodbrand et al. | |
| 2006/0111583 A1 | 5/2006 | Bender et al. | |
| 2006/0111588 A1 | 5/2006 | Bender et al. | |
| 2006/0115755 A1 | 6/2006 | Bender et al. | |
| 2006/0160002 A1 | 7/2006 | Qi et al. | |
| 2006/0222977 A1 | 10/2006 | Goodbrand et al. | |

FOREIGN PATENT DOCUMENTS

| | | |
|---|---|---|
| JP | A 57-128344 | 8/1982 |
| JP | A 63-65449 | 3/1988 |
| JP | A 4-15659 | 1/1992 |

OTHER PUBLICATIONS

Harris et al. "One-Pot synthesis of Unsymmetircal Triarylamines from Aniline", 2000, Journal of Organic Chemistry, vol. 65, pp. 5328-5331.*

Thayumanavan et al. "Synthesis of Unsysmmetrical Triarylamines for photonic Applications via One-Pot Palladium-Catalyzed Aminations", 1997, Chemistry of Materials, vol. 9.*

Adjabeng et al., "Novel Class of Tertiary Phosphine Ligands Based on a Phospha-adamantane Framework and Use in the Suzuki Cross-Coupling Reactions of Aryl Halides under Mild Conditions," American Chemical Society, Organic Letters, vol. 5, No. 6, 2003, pp. 953-955.

(Continued)

*Primary Examiner*—Yvonne Eyler
*Assistant Examiner*—Yate' K Cutliff
(74) *Attorney, Agent, or Firm*—Oliff & Berridge, PLC

(57) ABSTRACT

A process for forming a triarylamine compound, including reacting an aniline and an arylchloride in the presence of a ligated palladium catalyst and a base.

15 Claims, 1 Drawing Sheet

OTHER PUBLICATIONS

Brenstrum et al., "Phosphaadamantanes as Ligands for Palladium Catalyzed Cross-Coupling Chemistry: Library Synthesis, Characterization, and Screening in the Suzuki Coupling of Alkyl Halides Tosylates Containing β-Hydrogens with Boronic Acids and Alkylboranes," American Chemical Society, J. Org. Chem., vol. 69, No. 22, 2004, pp. 7635-7639.

McNulty et al., "Suzuki cross-coupling reactions of aryl halides in phosphonium salt ionic liquid under mild conditions," The Royal Society of Chemistry, Chem. Commun., 2002, pp. 1986-1987.

Harris et al., "One-Pot Synthesis of Unsymmetrical Triarylamines from Aniline Precursors," American Chemical Society, J. Org. Chem., vol. 65, No. 17, 2000, pp. 5327-5333.

U.S. Appl. No. 11/263,671, filed Nov. 1, 2005, Coggan et al.

U.S. Appl. No. 11/563,937, filed Nov. 27, 2006, Bender et al.

U.S. Appl. No. 11/563,873, filed Nov. 27, 2006, Bender et al.

* cited by examiner

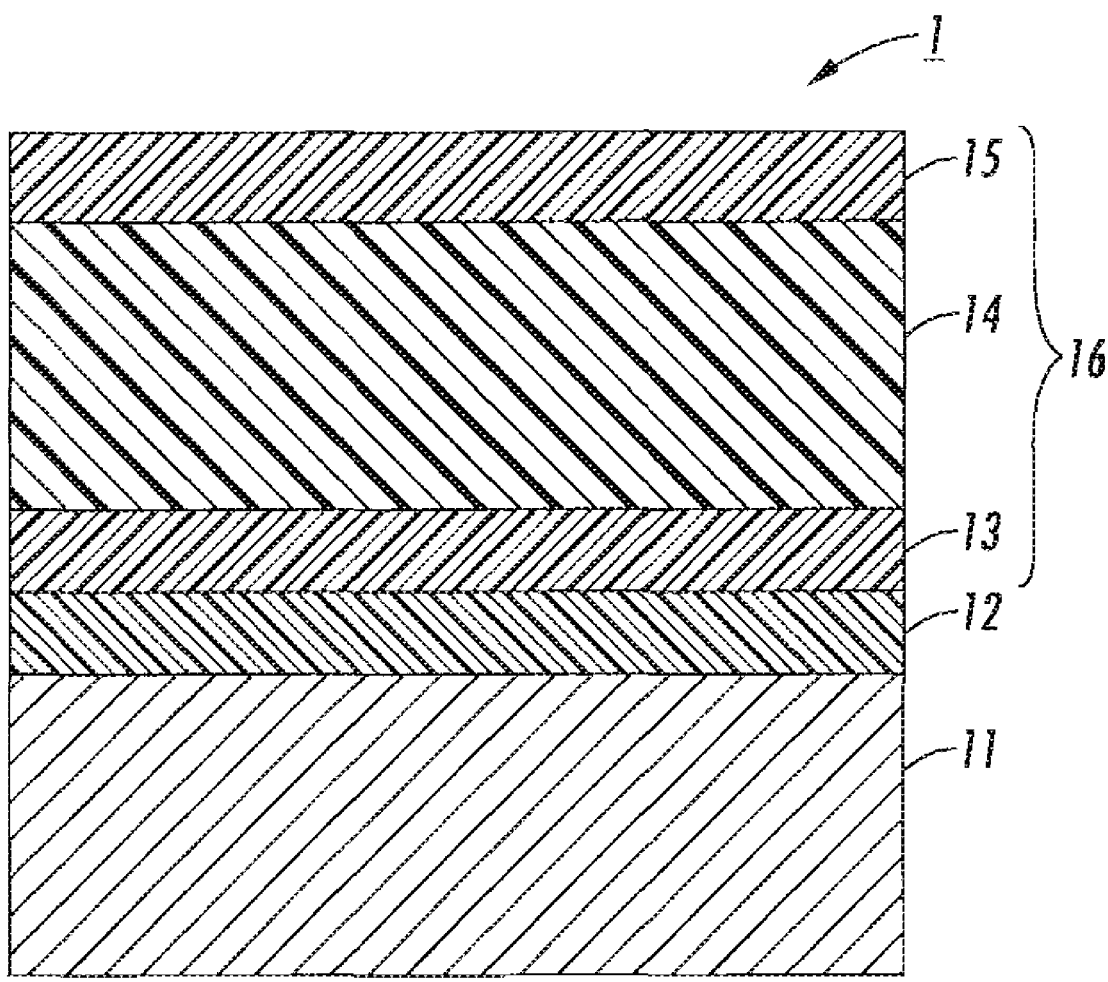

COST EFFECTIVE METHOD FOR SYNTHESIS OF TRIARYLAMINE COMPOUNDS FROM AN ANILINE AND AN ARYLCHLORIDE

TECHNICAL FIELD

This disclosure is generally directed to improved chemical processes for the synthesis of arylamine compounds, and to the use of such arylamine compounds in producing charge transport layers and overcoating layers for electrophotographic imaging members. In particular, this disclosure provides a method for producing a triarylamine molecule directly by the reaction of an aniline with an arylchloride compound.

RELATED APPLICATIONS

Commonly assigned, U.S. patent application Ser. No. 11/563,873 filed concurrently herewith, describes a method for the preparation of diarylamine molecules by the reaction of an aniline with an arylbromide compound using a ligated palladium catalyst in the presence of base.

Commonly assigned, U.S. patent application Ser. No. 11/563,937 filed concurrently herewith, describes an improved method for the preparation of derivatives of 4-aminobiphenyl using a ligated palladium catalyst in the presence of base.

Commonly assigned, U.S. patent application Ser. No. 11/263,671 filed Nov. 1, 2005, describes a process for the preparation of a tertiary arylamine compound, comprising reacting an arylhalide and an arylamine in an ionic liquid in the presence of a catalyst.

Commonly assigned, U.S. patent application Ser. No. 10/992,690 filed Nov. 22, 2004, describes a process for forming a tertiary arylamine compound, comprising reacting an arylbromide and an arylamine. For example, the application describes a process for forming N,N-diphenyl-4-aminobiphenyl, comprising reacting 4-bromobiphenyl and diphenylamine in the presence of a palladium-ligated catalyst.

Commonly assigned, U.S. patent application Ser. No. 10/992,687 filed Nov. 22, 2004, describes a process for forming a 4-aminobiphenyl derivative arylamine compound, comprising: (i) providing a first disubstituted 4-aminobiphenyl compound; (ii) optionally formylating the first disubstituted 4-aminobiphenyl compound to form a bisformyl substituted compound, where the first disubstituted 4-aminobiphenyl compound is not a bisformyl substituted compound; (iii) acidifying the bisformyl substituted compound to convert formyl functional groups into acid functional groups to form an acidified compound; and (iv) hydrogenating the acidified compound to saturate at least one unsaturated double bonds in the acidified compound, wherein there is provided a second disubstituted 4-aminobiphenyl compound.

Commonly assigned, U.S. patent application Ser. No. 10/992,658 filed Nov. 22, 2004, describes a process for forming a 4-aminobiphenyl derivative arylamine compound, comprising: (i) providing an iodinated organic compound; (ii) substituting the iodinated organic compound at carboxylic acid groups thereof to provide ester protecting groups; (iii) conducting an Ullman condensation reaction to convert the product of step (ii) into an arylamine compound; and (iv) conducting a Suzuki coupling reaction to add an additional phenyl group to the arylamine compound in the 4-position relative to the nitrogen, to provide the 4-aminobiphenyl derivative arylamine compound.

Commonly assigned, U.S. patent application Ser. No. 11/094,683 filed Mar. 31, 2005, describes a process for forming an anhydrous alkali earth salt of a dicarboxylic acid of an arylamine compound, comprising reacting a dicarboxylic acid of an arylamine compound with an anhydrous alkali earth salt. The application also discloses a process for forming a siloxane-containing hole-transport molecule, comprising: reacting a dicarboxylic acid of an arylamine compound with an anhydrous alkali earth salt to form an anhydrous dicarboxylic acid salt of the arylamine compound; and reacting the anhydrous dicarboxylic acid salt of the arylamine compound with a siloxane-containing compound.

Commonly assigned, U.S. patent application Ser. No. 10/998,585 filed Nov. 30, 2004, describes a silicon-containing layer for electrophotographic photoreceptors comprising: one or more siloxane-containing compound; and one or more siloxane-containing antioxidant; wherein the siloxane-containing antioxidant is at least one member selected from the group consisting of hindered-phenol antioxidants, hindered-amine antioxidants, thioether antioxidants and phosphite antioxidants.

Commonly assigned, U.S. patent application Ser. No. 11/034,713 filed Jan. 14, 2005, describes an electrophotographic photoreceptor comprising a charge-generating layer, a charge-transport layer, and an overcoat layer comprised of a crosslinked siloxane composite composition comprising at least one siloxane-containing compound and metal oxide particles.

Commonly assigned, U.S. patent application Ser. No. 10/709,193 filed Apr. 20, 2004, describes a process for preparing an aryl iodide compound, comprising: reacting an aryl halide compound with a metal iodide, a metal catalyst and a catalyst coordinating ligand in at least one solvent to form an aryl iodide; and purifying the aryl iodide; wherein the solvent is heated to reflux during the reacting; wherein an aryl iodide yield of at least about 75% is obtained; and wherein the aryl iodide has a purity of at least 90%.

The appropriate components and process aspects of each of the foregoing, such as the arylamine precursor materials and electrophotographic imaging members, may be selected for the present disclosure in embodiments thereof. The entire disclosures of the above-mentioned applications are totally incorporated herein by reference.

REFERENCES

JP-A-63-65449 (the term "JP-A" as used herein means an "unexamined published Japanese patent application"), discloses an electrophotographic photoreceptor in which fine silicone particles are added to a photosensitive layer, and also discloses that such addition of the fine silicone particles imparts lubricity to a surface of the photoreceptor.

Further, in forming a photosensitive layer, a method has been proposed in which a charge transport substance is dispersed in a binder polymer or a polymer precursor thereof, and then the binder polymer or the polymer precursor thereof is cured. JP-B-5-47104 (the term "JP-B" as used herein means an "examined Japanese patent publication") and JP-B-60-22347, disclose electrophotographic photoreceptors using silicone materials as the binder polymers or the polymer precursors thereof.

Furthermore, in order to improve mechanical strength of the electrophotographic photoreceptor, a protective layer is formed on the surface of the photosensitive layer in some cases. A cross-linkable resin is used as a material for the protective layer in many cases. However, the protective layer formed by the cross-linkable resin acts as an insulating layer, which impairs the photoelectric characteristics of the photoreceptor. For this reason, a method of dispersing a fine conductive metal oxide powder (JP-A-57-128344) or a charge-transport substance (JP-A-4-15659) in the protective layer and a method of reacting a charge-transport substance having a reactive functional group with a thermoplastic resin to form the protective layer have been proposed.

However, even the above-mentioned conventional electrophotographic photoreceptors are not necessarily sufficient in electrophotographic characteristics and durability, particularly when used in combination with a charger of the contact-charging system (contact charger) or a cleaning apparatus, such as a cleaning blade.

Further, when a photoreceptor is used in combination with a contact charger and a toner obtained by chemical polymerization (polymerization toner), a surface of the photoreceptor may become stained with a discharge product produced in contact charging or with polymerization toner that remains after a transport step. This staining can deteriorate image quality in some cases. Still further, use of a cleaning blade to remove discharge product or remaining toner adhered to the photoreceptor surface increases friction and abrasion between the surface of the photoreceptor and the cleaning blade, resulting in a tendency to cause damage to the surface of the photoreceptor, breakage of the blade or turning up of the blade.

Furthermore, in producing a photoreceptor, in addition to improvement in electrophotographic characteristics and durability, reducing production costs becomes an important problem. However, conventional electrophotographic photoreceptors also may have problems relating to coating defects such as orange peel appearances and hard spots.

The use of silicon-containing compounds in photoreceptor layers, including in photosensitive and protective layers, has been shown to increase the mechanical lifetime of electrophotographic photoreceptors, under charging conditions and scorotron charging conditions. For example, U.S. Patent Application Publication US 2004/0086794 to Yamada et al. discloses a photoreceptor having improved mechanical strength and stain resistance.

However, the above-mentioned conventional electrophotographic photoreceptor is not necessarily sufficient in electrophotographic characteristics and durability, particularly when such a photoreceptor is used in an environment of high heat and humidity.

Photoreceptors having low wear rates, such as those described in Yamada, also have low refresh rates. The low wear and refresh rates are a primary cause of image-deletion errors, particularly under conditions of high humidity and high temperature. U.S. Pat. No. 6,730,448 B2 to Yoshino et al. addresses this issue, disclosing photoreceptors having some improvement in image quality, fixing ability, even in an environment of high heat and humidity. However, there still remains a need for electrophotographic photoreceptors having high mechanical strength and improved electrophotographic characteristics and improved image deletion characteristics even under conditions of high temperature and high humidity.

The disclosures of each of the foregoing patents and publications, and the disclosures of any patents and publications cited below, are hereby totally incorporated by reference. The appropriate components and process aspects of the each of the foregoing patents and publications may also be selected for the present compositions and processes in embodiments thereof.

BACKGROUND

In electrophotography, an electrophotographic substrate containing a photoconductive insulating layer on a conductive layer is imaged by first uniformly electrostatically charging a surface of the substrate. The substrate is then exposed to a pattern of activating electromagnetic radiation, such as, for example, light. The electromagnetic radiation selectively dissipates charge in illuminated areas of the photoconductive insulating layer while leaving behind an electrostatic latent image in non-illuminated areas of the photoconductive insulating layer. This electrostatic latent image is then developed to form a visible image by depositing finely divided electroscopic marking particles on the surface of the photoconductive insulating layer. The resulting visible image is then transferred from the electrophotographic substrate to a necessary member, such as, for example, an intermediate-transfer member or a print substrate, such as paper. This image developing process can be repeated as many times as necessary with reusable photoconductive insulating layers.

In image-forming apparatus such as copiers, printers, and facsimiles, electrophotographic systems in which charging, exposure, development, transfer, etc., are carried out using electrophotographic photoreceptors have been widely employed. In such image-forming apparatus, there are ever-increasing demands for speeding up of image-formation processes, improvement in image quality, miniaturization and prolonged life of the apparatus, reduction in production cost and running cost, etc. Further, with recent advances in computers and communication technology, digital systems and color-image output systems have been applied also to the image-forming apparatus.

Electrophotographic imaging members (such as photoreceptors) are known. Electrophotographic imaging members are commonly used in electrophotographic processes having either a flexible belt or a rigid drum configuration. These electrophotographic imaging members sometimes comprise a photoconductive layer including a single layer or composite layers. These electrophotographic imaging members take many different forms. For example, layered photoresponsive imaging members are known in the art. U.S. Pat. No. 4,265,990 to Stolka et al. describes a layered photoreceptor having separate photogenerating and charge-transport layers. The photogenerating layer disclosed in Stolka is capable of photogenerating holes and injecting the photogenerated holes into the charge-transport layer. Thus, in the photoreceptors of Stolka, the photogenerating material generates electrons and holes when subjected to light.

More advanced photoconductive photoreceptors containing highly specialized component layers are also known. For example, a multi-layered photoreceptor employed in electrophotographic imaging systems sometimes includes one or more of a substrate, an undercoating layer, an intermediate layer, an optional hole- or charge-blocking layer, a charge-generating layer (including a photogenerating material in a binder) over an undercoating layer and/or a blocking layer, and a charge-transport layer (including a charge-transport material in a binder). Additional layers such as one or more overcoat layer or layers are also sometimes included.

In view of such a background, improvement in electrophotographic properties and durability, miniaturization, reduction in cost, and the like, in electrophotographic photoreceptors have been studied, and electrophotographic photoreceptors using various materials have been proposed.

Production of a number of arylamine compounds, such as arylamine compounds that are useful as charge-transport compounds in electrostatographic imaging devices and processes, often involves synthesis of intermediate materials, some of which generally are costly and/or time-consuming to produce, and some of which involve a multi-step process.

One such class of compounds are triarylamines. Certain triarylamine compounds may be produced by reaction of an aniline with an aryliodide under traditional Ullman conditions (copper catalyst, high temperature, long reaction time) or the so-called ligand-accelerated Ullman reaction that uses lower reaction temperatures but is still limited to the use of aryliodides (see Goodbrand et al: U.S. Pat. Nos. 5,902,901; 5,723,671; 5,723,669; 5,705,697; 5,654,482; and 5,648,542). Aryliodides tend to be very expensive reagents. Furthermore, both of these reactions usually require lengthy and costly purification processes.

Accordingly, improved processes providing safe, cost-effective, and efficient methods for triarylamine production are desired.

SUMMARY

The present disclosure addresses these and other needs, by providing an improved method for the preparation of triarylamines using a ligated palladium catalyst in the presence of base. More particularly, this disclosure provides a method of producing triarylamine molecules having two identical aryl rings by the reaction of an aniline with an arylchloride compound in the presence of a ligated palladium catalyst that is better suited for the industrial production of triarylamines.

In embodiments, the disclosure provides a process for forming a triarylamine compound, comprising reacting an aniline and an arylchloride in the presence of a ligated palladium catalyst and a base.

BRIEF DESCRIPTION OF THE DRAWING

The FIGURE is a schematic cross sectional view showing an embodiment of an electrophotographic photoreceptor of the disclosure.

EMBODIMENTS

This disclosure is not limited to particular embodiments described herein, and some components and processes may be varied by one of skill, based on this disclosure. The terminology used herein is for the purpose of describing particular embodiments only, and is not intended to be limiting.

In this specification and the claims that follow, singular forms such as "a," "an," and "the" include plural forms unless the content clearly dictates otherwise. In addition, reference may be made to a number of terms that shall be defined as follows:

The terms "hydrocarbon" and "alkane" refer, for example, to branched and unbranched molecules having the general formula $C_nH_{2n+2}$, wherein n is, for example, a number from 1 to about 100 or more, such as methane, ethane, n-propane, isopropane, n-butane, isobutane, tert-butane, octane, decane, tetradecane, hexadecane, eicosane, tetracosane, and the like. Alkanes may be substituted by replacing hydrogen atoms with one or more functional groups. The term "aliphatic" refers, for example, to straight-chain molecules, and may be used to describe acyclic, unbranched alkanes. The term "long-chain" refers, for example, to hydrocarbon chains in which n is a number of from about 8 to about 60, such as from about 20 to about 45 or from about 30 to about 40. The term "short-chain" refers, for example, to hydrocarbon chains in which n is an integer of from about 1 to about 7, such as from about 2 to about 5 or from about 3 to about 4.

The term "alkyl" refers, for example, to a branched or unbranched saturated hydrocarbon group, derived from an alkane and having the general formula $C_nH_{2n+1}$, wherein n is, for example, a number from 1 to about 100 or more, such as methyl, ethyl, n-propyl, isopropyl, n-butyl, isobutyl, tert-butyl, octyl, decyl, tetradecyl, hexadecyl, eicosyl, tetracosyl, and the like. The term "lower alkyl" refers, for example, to an alkyl group of from about 1 to about 12 carbon atoms. "Halogenated alkyl" refers, for example, to an alkyl group in which at least one hydrogen atom, and optionally all hydrogen atoms, is replaced by a halogen atom.

The term "aryl" refers, for example, to a monocyclic aromatic species of about 6 to about 20 carbon atoms or more, such as phenyl, naphthyl, anthrycyl, and the like. Optionally, these groups may be substituted with one or more independently selected substituents, including alkyl, alkenyl, alkoxy, hydroxyl and nitro groups.

The term "arylamine" refers, for example, to moieties containing both aryl and amine groups. Exemplary aralkylene groups have the structure Ar—NRR', in which Ar represents an aryl group and R and R' are groups that may be independently selected from hydrogen and substituted and unsubstituted alkyl, alkenyl, aryl, and other suitable functional groups. The term "triaylamine" refers, for example, to arylamine compounds having the general structure NArAr'Ar", in which Ar, Ar' and Ar" represent independently selected aryl groups.

The term "organic molecule" refers, for example, to any molecule that is made up predominantly of carbon and hydrogen, such as, for example, alkanes and arylamines. The term "heteroatom" refers, for example, to any atom other than carbon and hydrogen. Typical heteroatoms included in organic molecules include oxygen, nitrogen, sulfur and the like.

"Alcohol" refers, for example, to an alkyl moiety in which one or more of the hydrogen atoms has been replaced by an —OH group. The term "lower alcohol" refers, for example, to an alkyl group of about 1 to about 6 carbon atoms in which at least one, and optionally all, of the hydrogen atoms has been replaced by an —OH group.

"Amine" refers, for example, to an alkyl moiety in which one or more of the hydrogen atoms has been replaced by an —$NH_2$ group. The term "lower amine" refers, for example, to an alkyl group of about 1 to about 6 carbon atoms in which at least one, and optionally all, of the hydrogen atoms has been replaced by an —$NH_2$ group.

"Carbonyl compound" refers, for example, to an organic compound containing a carbonyl group, C=O, such as, for example, aldehydes, which have the general formula RCOH; ketones, which have the general formula RCOR'; carboxylic acids, which have the general formula RCOOH; and esters, which have the general formula RCOOR'.

The term "derivative" refers, for example, to compounds that are derived from another compound and maintain the same general structure as the compound from which they are derived. For example, saturated alcohols and saturated amines are derivatives of alkanes.

The term "homologous" refers, for example, to any number of series of organic compounds that have similar chemical properties and that differ by a constant relative molecular mass. For example, lower alcohols are a homologous series that includes $CH_3OH$, $CH_3CH_2OH$, $CH_3CH_2CH_2OH$, $CH_3(CH_2)_2CH_2OH$, $CH_3(CH_2)_3CH_2OH$ and $CH_3(CH_2)_4CH_2OH$, as well as isomers of these molecules.

The term "saturated" refers, for example, to compounds containing only single bonds. The term "unsaturated" refers, for example, to compounds that contain one or more double bonds and/or one or more triple bonds.

The term "reflux" refers, for example, to the process of boiling a liquid, condensing the vapor and returning the vapor to the original container. When a liquid is refluxed, the temperature of the boiling liquid remains constant. The term "boiling point" refers, for example, to the temperature at which the saturated vapor pressure of a liquid is equal to the external atmospheric pressure.

The terms "standard temperature" and "standard pressure" refer, for example, to the standard conditions used as a basis where properties vary with temperature and/or pressure. Standard temperature is 0° C.; standard pressure is 101,325 Pa or 760.0 mmHg. The term "room temperature" refers, for example, to temperatures in a range of from about 20° C. to about 25° C.

The terms "high temperature environment" and "high temperature conditions" refer, for example, to an atmosphere in which the temperature is at least about 28 or about 30° C., and may be as high as about 300° C. The terms "high humidity environment" and "high humidity conditions" refer, for example, to an atmosphere in which the relative humidity is at least about 75 or about 80%.

The terms "one or more" and "at least one" herein mean that the description includes instances in which one of the subsequently described circumstances occurs, and that the description includes instances in which more than one of the subsequently described circumstances occurs.

An improved process for producing triarylamines directly from an aniline is to react an arylchloride with an aniline compound in the presence of a suitable catalyst. For example, 3,4-dimethylaniline can be rapidly reacted with chlorobenzene to form 3,4-dimethyl-N,N-diphenylaniline using palladium acetate ligated with 2,4,6-trioxa-1,3,5,7-tetramethyl-8-phosphaadamantane, which is manufactured as Cytop-216 (Cytec Industries), and sodium t-pentoxide base. This reaction proceeds rapidly, in about 4 to 8 hours to produce the desired triarylamine.

The results surrounding this process were very unexpected in that the reaction of an aniline with an arylchloride compound in the presence of a ligated palladium catalyst proceeded easily to produce triarylamine compound. The same reaction conditions utilizing an arylbromide or an aryliodide instead of an arylchloride do not exclusively produce triarylamine. Therefore, this process is very practical and applicable to the preparation of triarylamines on an industrial scale since a single-step reaction produces a triarylamine in a short reaction time with high purity crude products that require little purification. This shorter, improved process is now described in detail.

According to the processes of the present invention, an aniline and an arylchloride are used as starting materials. In embodiments, the reaction of the present invention, including the starting materials and final product, can generally be represented as follows:

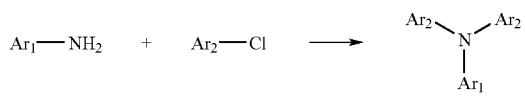

Thus, in this embodiment, an aniline is reacted with an arylchloride to produce a triarylamine having two identical aryl rings.

In this reaction scheme, the aniline can be any suitable aniline, depending on the desired final product. Thus, for example, in the above reaction scheme, Ar1 can be any known substituted or unsubstituted aromatic component or a substituted or unsubstituted aryl group having from 2 to about 15 conjugate bonded or fused benzene rings and could include, but is not limited to, phenyl, naphthyl, anthryl, phenanthryl, and the like. The substituents on Ar1 can be suitably selected to represent hydrogen, a halogen, an alkyl group having from 1 to about 20 carbon atoms, a hydrocarbon radical having from 1 to about 20 carbon atoms, an aryl group optionally substituted by one or more alkyl groups, an alkyl group containing a heteroatom such as oxygen, nitrogen, sulfur, and the like, having from 1 to about 20 carbon atoms, a hydrocarbon radical containing a heteroatom such as oxygen, nitrogen, sulfur, and the like, having from 1 to about 20 carbon atoms, an aryl group containing a heteroatom such as oxygen, nitrogen, sulfur, and the like, optionally substituted by one or more alkyl groups, and the like.

Likewise, in this reaction scheme, the arylchloride can be any suitable arylchloride, depending upon the desired final product. Thus, for example, in the above reaction scheme, Ar2 can be any known substituted or unsubstituted aromatic component or a substituted or unsubstituted aryl group having from 2 to about 15 conjugate bonded or fused benzene rings and could include, but is not limited to, phenyl, naphthyl, anthryl, phenanthryl, and the like. The substituents on Ar2 can be suitably selected to represent hydrogen, a halogen, an alkyl group having from 1 to about 20 carbon atoms, a hydrocarbon radical having from 1 to about 20 carbon atoms, an aryl group optionally substituted by one or more alkyl groups, an alkyl group containing a heteroatom such as oxygen, nitrogen, sulfur, and the like, having from 1 to about 20 carbon atoms, a hydrocarbon radical containing a heteroatom such as oxygen, nitrogen, sulfur, and the like, having from 1 to about 20 carbon atoms, an aryl group containing a heteroatom such as oxygen, nitrogen, sulfur, and the like, optionally substituted by one or more alkyl groups, and the like.

The reactants are reacted in the presence of a suitable catalyst. Although not particularly limited, suitable catalysts are those that are known or discovered to be useful for formation of nitrogen-carbon bonds. For example, suitable catalysts include ligated palladium catalysts, such as those disclosed by Buchwald et al. and Hartwig et al. (see, e.g., *J. Org. Chem.* 2000, 65, 5327-5333, the entire disclosure of which is incorporated herein by reference).

In an embodiment of the present invention, an example of a suitable catalyst is palladium acetate ligated with tri-t-butylphosphine in the presence of a base. In another embodiment of the present invention, an example of a suitable catalyst is palladium acetate ligated with a phospha-adamantane molecule given by structural formula (I):

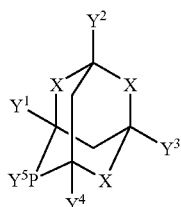

(I)

in the presence of a base, where each X individually represents either $CH_2$ or an oxygen atom; $Y^1$, $Y^2$, $Y^3$, and $Y^4$ each individually represent a substituted or unsubstituted, straight or branched, alkyl, alkenyl, or alkynyl group having from 1 to about 10 carbon atoms, such as from 1 to about 5, or from 1 to about 3 carbon atoms; and $Y^5$ represents hydrogen, a substituted or unsubstituted alkyl group, or an aryl group. One specific molecule given by formula (I) is 2,4,6-trioxa-1,3,5,7-tetramethyl-8-phosphaadamantane, which is manufactured as Cytop-216 (Cytec Industries). However, it will be apparent to those skilled in the art that other ligands, such as any tertiary phosphine ligand such as biaryldialkylphosphine or trialkyl phosphine ligands, could also be used to produce suitable results (from the point of view of conversion and yield), and thus would be suitable to ligate palladium or other metals and thus act as catalysts for the process described in this disclosure.

Any suitable base may be used in embodiments, such as an alkaline hydroxide or an alkaline alkoxide and the like. Exemplary bases that may be used in embodiments include bases having the general formula MOR, in which O is oxygen, M is a metal atom, and R is a hydrogen or an alkyl group. M is a metal selected from potassium, sodium, lithium, calcium, magnesium and the like; and R is a hydrogen or a straight or branched alkyl group selected from methyl, ethyl, propyl, butyl, pentyl, hexyl, heptyl, octyl, nonyl, and decyl groups, such as methyl, ethyl, n-propyl, isopropyl, n-butyl, isobutyl, tert-butyl, octyl, decyl and the like. Suitable bases include potassium tert-butoxide salt, sodium tert-butoxide, and sodium tert-pentoxide.

The reaction is carried out in the presence of the catalyst, and can be conducted in continuous mode. However, the reaction may be conducted in batch mode. For example, the reaction can be carried out for a period of from about 2 to about 10 hours or more, such as a reaction time of from about 4 to about 6 hours.

The reaction can be carried out in a suitable solvent, such as toluene, decane, other hydrocarbon solvents (either aromatic or saturated hydrocarbons), or mixtures thereof. The choice of solvent can be decided based on the solubility of the starting materials, intermediates, and final products, and will be readily apparent or within routine experimentation to those skilled in the art. Furthermore the choice of solvent can be decided based on the desired operating temperature range. The described process is exothermic and precautions should be taken to ensure that the solvent chosen is capable of dispersing the produced heat by, for example, refluxing and cooling at such a rate so as to control the exotherm. The reaction should be conducted under an atmosphere of inert gas (such as nitrogen or argon) so as to preclude deactivation of catalyst or base by oxygen or atmospheric moisture.

After the reaction is completed, suitable separation, filtration, and/or purification processes can be conducted, as desired to a desired purity level. For example, the desired triarylamine product can be subjected to conventional organic washing steps, can be separated, can be decolorized (if necessary), treated with known absorbents (such as silica, alumina, and clays, if necessary) and the like. The final product can be isolated, for example, by a suitable recrystallization procedure. The final product can also be dried, for example, by air drying, vacuum drying, or the like. All of these procedures are conventional and will be apparent to those skilled in the art.

The triaylamine produced by this process can be further processed and/or reacted to provide other compounds for their separate use. For example, the triarylamine can be further processed and/or reacted to provide charge-transport materials or other compounds useful in such electrostatographic imaging member. An exemplary electrostatographic imaging member will now be described in greater detail.

The FIGURE is a cross-sectional view schematically showing an embodiment of the electrophotographic photoreceptor of the disclosure. The electrophotographic photoreceptor 1 shown in the FIGURE is a function-separation-type photoreceptor in which a charge-generation layer 13 and a charge-transport layer 14 are separately provided. That is, an underlayer 12, the charge-generation layer 13, the charge transport layer 14 and a protective layer 15 are laminated onto a conductive support 11 to form a photosensitive layer 16. The protective layer 15 contains a resin soluble in the liquid component contained in the coating solution used for formation of this layer and the silicon compound. The various layers of the photoreceptor are generally known, and are described in detail in the above-mentioned commonly owned and co-pending In electrophotographic photoreceptors of embodiments, the photoreceptors can include various layers such as undercoating layers, charge generating layers, charge transport layers, overcoat layers, and the like.

The charge transport layer generally comprises a charge transporting small molecule dissolved or molecularly dispersed in a film forming electrically inert polymer such as a polycarbonate. The term "dissolved" as employed herein is defined as forming a solution in which the small molecule is dissolved in the polymer to form a homogeneous phase. The expression "molecularly dispersed" as used herein is defined as a charge transporting small molecule dispersed in the polymer, the small molecules being dispersed in the polymer on a molecular scale. Any suitable charge transporting or electrically active small molecule may be employed in the charge transport layer. The expression charge transporting "small molecule" is defined herein as a monomer that allows the free charge photogenerated in the transport layer to be transported across the transport layer. Typical charge transporting small molecules include, for example, pyrazolines such as 1-phenyl-3-(4'-diethylamino styryl)-5-(4"-diethylamino phenyl)pyrazoline, diamines such as N,N'-diphenyl-N,N'-bis(3-methylphenyl)-(1,1'-biphenyl)-4,4'-diamine, hydrazones such as N-phenyl-N-methyl-3-(9-ethyl)carbazyl hydrazone and 4-diethyl amino benzaldehyde-1,2-diphenyl hydrazone, and oxadiazoles such as 2,5-bis (4-N,N'-diethylaminophenyl)-1,2,4-oxadiazole, stilbenes and the like. A small molecule charge transporting compound that permits injection of holes from the pigment into the charge generating layer with high efficiency and transports them across the charge transport layer with very short transit times is N,N'-diphenyl-N,N'-bis(3-methylphenyl)-(1,1'-biphenyl)-4,4'-diamine. If desired, the charge transport material in the charge transport layer may comprise a polymeric charge transport material or a combination of a small molecule charge transport material and a polymeric charge transport material.

Any suitable electrically inactive resin binder insoluble in the alcohol solvent used to apply an optional overcoat layer may be employed in the charge transport layer. Typical inactive resin binders include polycarbonate resin, polyester, polyarylate, polysulfone, and the like. Molecular weights can vary, for example, from about 20,000 to about 150,000. Exemplary binders include polycarbonates such as poly(4,4'-isopropylidene-diphenylene)carbonate (also referred to as bisphenol-A-polycarbonate, poly(4,4'-cyclohexylidine-diphenylene) carbonate (referred to as a bisphenol-Z polycarbonate), poly(4,4'-isopropylidene-3,3'-dimethyl-diphenyl)carbonate (also referred to as bisphenol-C-polycarbonate) and the like. Any suitable charge transporting polymer may also be utilized in the charge transporting layer. The charge transporting polymer should be insoluble in any solvent employed to apply the subsequent overcoat layer described below, such as an alcohol solvent. These electrically active charge transporting polymeric materials should be capable of supporting the injection of photogenerated holes from the charge generation material and be incapable of allowing the transport of these holes therethrough.

Any suitable and conventional technique may be utilized to mix and thereafter apply the charge transport layer coating mixture to the charge generating layer. Typical application techniques include spraying, dip coating, roll coating, wire wound rod coating, and the like. Drying of the deposited coating may be effected by any suitable conventional technique such as oven drying, infra red radiation drying, air drying, and the like.

Generally, the thickness of the charge transport layer is between about 10 and about 50 micrometers, but thicknesses outside this range can also be used. The hole transport layer should be an insulator to the extent that the electrostatic charge placed on the hole transport layer is not conducted in the absence of illumination at a rate sufficient to prevent formation and retention of an electrostatic latent image thereon. In general, the ratio of the thickness of the hole transport layer to the charge generator layers is desirably maintained from about 2:1 to 200:1 and in some instances as great as 400:1. The charge transport layer, is substantially non-absorbing to visible light or radiation in the region of intended use but is electrically "active" in that allows the injection of photogenerated holes from the photoconductive layer, i.e., charge generation layer, and allows these holes to be transported through itself to selectively discharge a surface charge on the surface of the active layer.

To improve photoreceptor wear resistance, a protective overcoat layer can be provided over the charge transport layer (or other underlying layer). Various overcoating layers are known in the art, and can be used as long as the functional properties of the photoreceptor are not adversely affected. The overcoating layers of embodiments can be a silicon overcoat layer, which can comprise one or more silicon compounds, a resin, and a charge transport molecule such as an arylamine.

In embodiments, the resin may be a resin soluble in a liquid component in a coating solution used for formation of a silicon overcoat layer. Such a resin soluble in the liquid component may be selected based upon the kind of liquid component. For example, if the coating solution contains an alcoholic solvent, a polyvinyl acetal resin such as a polyvinyl butyral resin, a polyvinyl formal resin or a partially acetalized polyvinyl acetal resin in which butyral is partially modified with formal or acetoacetal, a polyamide resin, a cellulose resin such as ethyl cellulose and a phenol resin may be suitably chosen as the alcohol-soluble resins. These resins may be used either alone or as a combination of two or more resins. Of the above-mentioned resins, the polyvinyl acetal resin is particularly suitable in embodiments in terms of electric characteristics.

In embodiments, the weight-average molecular weight of the resin soluble in the liquid component may be from about 2,000 to about 1,000,000, such as from about 5,000 to about 50,000. When the weight-average molecular weight is less than about 2,000, enhancing discharge gas resistance, mechanical strength, scratch resistance, particle dispersibility, etc., tend to become insufficient. However, when the weight-average molecular weight exceeds about 1,000,000, the resin solubility in the coating solution decreases, and the amount of resin added to the coating solution may be limited and poor film formation in the production of the photosensitive layer may result.

Further, the amount of the resin soluble in the liquid component may be, in embodiments, from about 0.1 to about 15% by weight, or from about 0.5 to about 10% by weight, based on the total amount of the coating solution. When the amount added is less than 0.1% by weight, enhancing discharge gas resistance, mechanical strength, scratch resistance, particle dispersibility, etc. tend to become insufficient. However, if the amount of the resin soluble in the liquid component exceeds about 15% by weight, there is a tendency for formation of indistinct images when the electrophotographic photoreceptor of the disclosure is used at high temperature and high humidity.

There is no particular limitation on the silicon compound used in embodiments of the disclosure, as long as it has at least one silicon atom. However, a compound having two or more silicon atoms in its molecule may be used in embodiments. The use of the compound having two or more silicon atoms in its molecule allows both the strength and image quality of the electrophotographic photoreceptor to be achieved at higher levels.

Various fine particles can also be added to the silicon compound-containing layer. The fine particles may be used either alone or as a combination of two or more such fine particles. Non-limiting examples of the fine particles include fine particles containing silicon, such as fine particles containing silicon as a constituent element, and specifically include colloidal silica and fine silicone particles.

Colloidal silica used in embodiments as the fine particles containing silicon in the disclosure is selected from an acidic or alkaline aqueous dispersion of the fine particles having an average particle size of 1 to 100 nm, or 10 to 30 nm, and a dispersion of the fine particles in an organic solvent such as an alcohol, a ketone or an ester, and generally, commercially available particles can be used.

There is no particular limitation on the solid content of colloidal silica in a top surface layer of the electrophotographic photoreceptor of embodiments. However, in embodiments, colloidal silica may be included in amounts of from about 1 to about 50% by weight, such as from about 5 to about 30% by weight, based on the total solid content of the top surface layer, in terms of film forming properties, electric characteristics and strength.

The fine silicone particles used as the fine particles containing silicon in the disclosure are selected from silicone resin particles, silicone rubber particles and silica particles surface-treated with silicone, which are spherical and have an average particle size of from about 1 to 500 nm, such as from about 10 to about 100 nm, and generally, commercially available particles can be used in embodiments.

In embodiments, the fine silicone particles are small-sized particles that are chemically inactive and excellent in dispersibility in a resin, and further are low in content as may be necessary for obtaining sufficient characteristics. Accordingly, the surface properties of the electrophotographic photoreceptor can be improved without inhibition of the crosslinking reaction. That is to say, fine silicone particles improve the lubricity and water repellency of surfaces of electrophotographic photoreceptors where incorporated into strong crosslinked structures, which may then be able to maintain good wear resistance and stain adhesion resistance for a long period of time. The content of the fine silicone particles in the silicon compound-containing layer of embodiments may be from about 0.1 to about 20% by weight, such as from about 0.5 to about 10% by weight, based on the total solid content of the silicon compound-containing layer.

Other fine particles that may be used in embodiments include fine fluorine-based particles such as ethylene tetrafluoride, ethylene trifluoride, propylene hexafluoride, vinyl fluoride and vinylidene fluoride, and semiconductive metal oxides such as $ZnO$—$Al_2O_3$, $SnO_2$—$Sb_2O_3$, $In_2O_3$—$SnO_2$, $ZnO$—$TiO_2$, $MgO$—$Al_2O_3$, $FeO$—$TiO_2$, $TiO_2$, $SnO_2$, $In_2O_3$, $ZnO$ and $MgO$.

In conventional electrophotographic photoreceptors, when the above-mentioned fine particles are contained in the photosensitive layer, the compatibility of the fine particles with a charge transport substance or a binding resin may become insufficient, which causes layer separation in the photosensitive layer, and thus the formation of an opaque film. As a result, the electric characteristics have deteriorated in some cases. In contrast, the silicon compound-containing layer of embodiments (a charge transport layer in this case) may contain the resin soluble in the liquid component in the coating solution used for formation of this layer and the silicon compound, thereby improving the dispersibility of the fine particles in the silicon compound-containing layer. Accordingly, the pot life of the coating solution can be sufficiently prolonged, and it becomes possible to prevent deterioration of the electric characteristics.

Further, an additive such as a plasticizer, a surface modifier, an antioxidant, or an agent for preventing deterioration by light can also be used in the silicon compound-containing layer of embodiments. Non-limiting examples of plasticizers that may be used in embodiments include, for example, biphenyl, biphenyl chloride, terphenyl, dibutyl phthalate, diethylene glycol phthalate, dioctyl phthalate, triphenylphosphoric acid, methylnaphthalene, benzophenone, chlorinated paraffin, polypropylene, polystyrene, and various fluorohydrocarbons.

The antioxidants may include an antioxidant having a hindered-phenol, hindered-amine, thioether, or phosphite partial structure. This is effective for improvement of potential stability and image quality in environmental variation. The antioxidants include an antioxidant having a hindered-phenol, hindered-amine, thioether or phosphite partial structure. This is effective for improvement of potential stability and image quality in environmental variation.

There is no particular limitation on the thickness of the silicon-containing layer, however, in embodiments, the silicon-containing layer may be from about 2 to about 5 μm in thickness, such as from about 2.7 to about 3.2 μm in thickness.

The electrophotographic photoreceptor of embodiments may be either a function-separation-type photoreceptor, in which a layer containing a charge-generation substance (charge-generation layer) and a layer containing a charge-transport substance (charge-transport layer) are separately provided, or a monolayer-type photoreceptor, in which both the charge-generation layer and the charge-transport layer are contained in the same layer.

Specific examples are described in detail below. These examples are intended to be illustrative, and the materials, conditions, and process parameters set forth in these exemplary embodiments are not limiting. All parts and percentages are by weight unless otherwise indicated.

EXAMPLE

The invention will be illustrated in greater detail with reference to the following Example, but the invention should not be construed as being limited thereto. In the following example, all the "parts" are given by weight unless otherwise indicated.

Preparation of 3,4-dimethyl-N,N-diphenylaniline

In a 500 mL round bottom flask was placed palladium acetate (370 mg), and Cytop-216 (365 mg) and were stirred in chlorobenzene (50 mL) for at least 30 minutes. To this mixture was added, in order, 3,4-dimethylaniline (20 g), chlorobenzene (100 mL) and sodium tert-pentoxide (40 g), and the resulting mixture heated to 130° C. for between 6 and 18 hours after which time HPLC analysis can confirm complete conversion to the desired triarylamine. Between 50 mL and 100 mL of chlorobenzene was distilled from the reaction mixture. The mixture was cooled to room temperature and methanol (200 mL) and water (20 mL) were added. The precipitate was collected by filtration and dried overnight under vacuum. The yield was >75% and the purity was >99% as confirmed by HPLC and NMR.

While this procedure represents a preferred example done at lab scale, it has also been observed that the reaction need not be carried out in neat arylchloride to be a success. Regardless of whether the arylchloride is present in reagent amounts (1.0-1.2 mol equivalents), mixed 50/50 (vol/vol) with a cosolvent (xylene), or neat, the reaction proceeds to completion after heating at 130° C. overnight.

It will be appreciated that various of the above-discussed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:

1. A process for forming a triaylamine compound, comprising:
   reacting an aniline and an arylchloride in the presence of a palladium ligated catalyst and a base;
   wherein the palladium ligated catalyst is a palladium acetate ligated with a molecule given by structural formula (I):

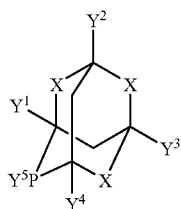
(I)

wherein:
  each X individually represents either $CH_2$ or an oxygen atom;
  $Y^1$, $Y^2$, $Y^3$, and $Y^4$ each individually represent a substituted or unsubstituted, straight or branched, alkyl, alkenyl, or alkynyl group, having from 1 to about 10 carbon atoms; and
  $Y^5$ represents hydrogen, a substituted or unsubstituted alkyl group, or an aryl group.

2. The process according to claim 1, wherein the aniline, the arylchloride, and the triarylamine, are represented as follows:

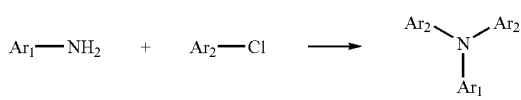

wherein:
  Ar1 and Ar2, which can be the same or different, are selected from the group consisting of substituted or unsubstituted aromatic components, and substituted or unsubstituted aryl groups having from 2 to about 15 conjugate bonded or fused benzene rings;
  wherein a substituent on the aryl groups Ar1 and Ar2 is selected from the group consisting of hydrogen, a halogen, an alkyl group having from 1 to about 20 carbon atoms, a hydrocarbon radical having from 1 to about 20 carbon atoms, an aryl group, an aryl group substituted by one or more alkyl groups, an alkyl group containing a heteroatom and having from 1 to about 20 carbon atoms, a hydrocarbon radical containing a heteroatom and having from 1 to about 20 carbon atoms, an aryl group containing a heteroatom, and an aryl group containing a heteroatom substituted by one or more alkyl groups.

3. The process according to claim 1, wherein the process is conducted in batch mode.

4. The process according to claim 1, wherein the process is conducted in continuous mode.

5. The process according to claim 1, wherein the process is carried out in a time of from about 2 to about 10 hours.

6. The process according to claim 1, wherein the process is carried out in a solvent.

7. The process according to claim 6, wherein the solvent is toluene.

8. The process according to claim 1, wherein the process is carried out under an inert atmosphere.

9. The process according to claim 1, wherein the base is represented by a general formula MOR, where:
  O is oxygen;
  M is a metal selected from the group consisting of potassium, sodium, lithium, calcium, magnesium; and
  R is a hydrogen or a straight or branched alkyl group selected from the group consisting of methyl, ethyl, propyl, butyl, pentyl, hexyl, heptyl, octyl, nonyl, and decyl groups.

10. The process according to claim 1, wherein the base is potassium tert-butoxide salt.

11. The process according to claim 1, wherein the base is sodium t-pentoxide.

12. The process according to claim 1, wherein the base is sodium t-butoxide.

13. The process according to claim 1, wherein the molecule given by structural formula (I) is 2,4,6-trioxa-1,3,5,7-tetramethyl-8-phosphaadamantane.

14. The process according to claim 1, wherein $Y^1$, $Y^2$, $Y^3$, and $Y^4$ each individually represent a substituted or unsubstituted, straight or branched, alkyl, alkenyl, or alkynyl group, having from 1 to about 6 carbon atoms.

15. The process according to claim 1, wherein $Y^1$, $Y^2$, $Y^3$, and $Y^4$ each individually represent a substituted or unsubstituted, straight or branched, alkyl, alkenyl, or alkynyl group, having from 1 to about 3 carbon atoms.

* * * * *